(12) United States Patent
Izrailit et al.

(10) Patent No.: US 9,797,850 B2
(45) Date of Patent: Oct. 24, 2017

(54) SENSOR FOR WEAR MEASUREMENT, METHOD OF MAKING, AND METHOD OF OPERATING SAME

(71) Applicant: NanoLab, Inc., Waltham, MA (US)

(72) Inventors: Iosif Izrailit, Newton, MA (US); David L. Carnahan, Needham, MA (US)

( * ) Notice: Subject to any disclaimer, the term of this patent is extended or adjusted under 35 U.S.C. 154(b) by 431 days.

(21) Appl. No.: 14/054,447

(22) Filed: Oct. 15, 2013

(65) Prior Publication Data

US 2014/0103940 A1   Apr. 17, 2014

Related U.S. Application Data

(60) Provisional application No. 61/713,735, filed on Oct. 15, 2012.

(51) Int. Cl.
| | |
|---|---|
| *G01N 27/02* | (2006.01) |
| *G01N 27/22* | (2006.01) |
| *F16C 17/24* | (2006.01) |
| *G01N 3/56* | (2006.01) |
| *F16C 17/02* | (2006.01) |
| *F16C 23/04* | (2006.01) |

(52) U.S. Cl.
CPC .......... *G01N 27/02* (2013.01); *F16C 17/246* (2013.01); *G01N 27/22* (2013.01); *G01N 27/221* (2013.01); *F16C 17/02* (2013.01); *F16C 23/043* (2013.01); *G01N 3/56* (2013.01)

(58) Field of Classification Search
None
See application file for complete search history.

(56) References Cited

U.S. PATENT DOCUMENTS

| | | | |
|---|---|---|---|
| 3,950,599 A | 4/1976 | Board, Jr. | |
| 4,006,051 A | 2/1977 | Board, Jr. | |
| 4,122,388 A * | 10/1978 | Bernasconi | G01R 19/145 324/510 |
| 6,324,899 B1 | 12/2001 | Discenzo | |
| 7,166,354 B2 | 1/2007 | Tsunashima et al. | |
| 7,270,890 B2 * | 9/2007 | Sabol | C23C 4/18 416/61 |
| 7,354,877 B2 | 4/2008 | Rosenberger et al. | |
| 7,551,288 B1 | 6/2009 | Discenzo | |
| 2005/0109090 A1 | 5/2005 | Pfeffer | |
| 2008/0199247 A1 | 8/2008 | Spratte et al. | |
| 2009/0219040 A1 | 9/2009 | Shinde et al. | |
| 2011/0075382 A1 | 3/2011 | Mackey et al. | |
| 2012/0106095 A1 | 5/2012 | Daniel | |
| 2014/0103942 A1 | 4/2014 | Izrailit et al. | |

* cited by examiner

*Primary Examiner* — Paul West
*Assistant Examiner* — Mark A Shabman
(74) *Attorney, Agent, or Firm* — Pandiscio & Pandiscio

(57) ABSTRACT

A wear sensor comprising:
an insulating substrate having a top surface and a bottom surface;
a conductive electrode formed on said top surface of said insulating substrate;
an insulating wear lining material having a first side secured to said top surface of said insulating substrate and conductive electrode, an opposite second side that will be worn down by relative motion between the wear sensor and a moving component; and
one or more contact points where the electrical properties between the electrode and the moving component can be measured.

15 Claims, 9 Drawing Sheets

FIG. 9A  FIG. 9B  FIG. 9C

SENSOR FOR WEAR MEASUREMENT, METHOD OF MAKING, AND METHOD OF OPERATING SAME

REFERENCE TO PENDING PRIOR PATENT APPLICATION

This patent application claims benefit of prior U.S. Provisional Patent Application Ser. No. 61/713,735, filed Oct. 15, 2012 by Iosif Izrailit et al. for SENSOR FOR WEAR MEASUREMENT, METHOD OF MAKING, AND METHOD OF OPERATING SAME, which patent application is hereby incorporated herein by reference.

FIELD OF THE INVENTION

This invention relates to wear sensing devices in general, and more particularly to a sensor suited to the measurement of wear in bearings that employ a low friction wear lining material, instead of balls or rollers to support the load. More particularly, the invention relates to the electrical measurement of capacitance or other electrical impedance parameters between a movable surface and an electrode, which may be positioned within or on the back side of the wear liner, and its correlation to wear.

BACKGROUND OF THE INVENTION

Condition based maintenance programs rely upon inspection to identify those parts that are nearing their end of life. Bearings are no exception to this rule. The replacement of a bearing before it is fully worn out may be wasteful, but waiting too long to replace a bearing can be catastrophic in some applications, particularly with rotorcraft and aircraft. It is known in the art to place sensors inside a bearing to measure wear. Discenzo (U.S. Pat. No. 7,551,288) disclosed a system for monitoring bearing wear that employed an optical fiber embedded in the bearing and operatively coupled to an interferometric system. Such a system will measure wear at only one point, and that point may not coincide with the area of maximum wear. Bearings with multiple optical fibers were disclosed to try to remedy this defect, but the overall complexity required for this measurement rendered the solution cost prohibitive.

It is the goal of this invention to provide a sensor that will detect wear in any location within the bearing, and enable timely replacement, using a cost effective method.

SUMMARY OF THE INVENTION

These and other objects are addressed by the provision and use of a novel insulating wear liner with a sensor for detecting wear on a bearing. More particularly, a sensor having an electrode can be inserted in, or on the back of, a wear liner in a bearing for monitoring the wear of the wear liner by monitoring the impedance parameters such as capacitance, inductance, and resistance, or a combination thereof, between the electrode and a movable component, such as a shaft.

In one form of the present invention, there is provided a wear sensor comprising:
an insulating substrate having a top surface and a bottom surface;
a conductive electrode formed on said top surface of said insulating substrate;
an insulating wear lining material having a first side secured to said top surface of said insulating substrate and conductive electrode, an opposite second side that will be worn down by relative motion between the wear sensor and a moving component; and
one or more contact points where the electrical properties between the electrode and the moving component can be measured.

In another form of the present invention, there is provided a sensor comprising:
an electrode trace patterned on the surface of an insulating substrate;
a layer of insulating material deposited on top of the electrode trace, wherein the layer of insulating material comprises a wear resistant material; and
an electrical lead for measuring the capacitance between the electrode trace and an opposing metallic surface that wears upon said wear resistant material.

In another form of the present invention, there is provided a wear sensor comprising:
an insulating substrate having a top surface and a bottom surface;
a conductive electrode patterned on said top surface of said insulating substrate;
a conductive wear lining material having a first side secured to said top surface of said insulating substrate and conductive electrode, and an opposite second side that will be worn down by relative motion between the sensor and a moving component;
one or more contact points where the electrical properties between the electrode trace and the moving component can be measured.

In another form of the present invention, there is provided a method for sensing wear in a bearing for a moving component, the method comprising:
providing a wear sensor comprising:
an insulating substrate having a top surface and a bottom surface;
a conductive electrode formed on said top surface of said insulating substrate;
an insulating wear lining material having a first side secured to said top surface of said insulating substrate and conductive electrode, an opposite second side that will be worn down by relative motion between the wear sensor and a moving component; and
one or more contact points where the electrical properties between the electrode and the moving component can be measured;
positioning the wear sensor inside of a wear liner of a bearing; and
measuring at least one electrical property between the electrode and the moving component so as to determine the wear in the bearing.

BRIEF DESCRIPTION OF THE DRAWINGS

These and other objects, features and advantages of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

The present invention comprises an insulating wear liner with a sensor that is positioned either within the liner or placed on the non-wearing surface of the liner. The sensor is comprised of a conductive electrode and one or more pads for interrogating the electrical properties of the sensor. The liner is situated between the race and the moving part.

By way of example but not limitation, a sensor may be positioned inside of the wear liner of a sleeve bearing, and the capacitance between the wear liner and the shaft can be calculated in the new condition of the shaft and wear liner, and after wear by a shaft.

Figure 1A:
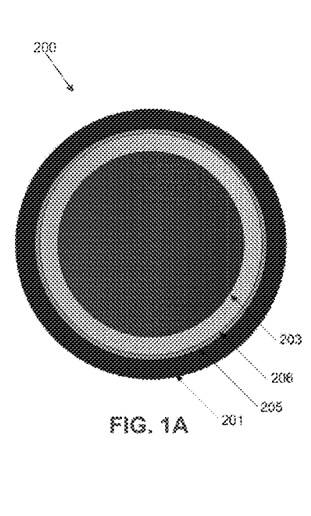
FIG. 1A illustrates a new sleeve bearing with a sensor inserted into a wear liner in accordance with the present invention.

Looking now at FIG. 1A, FIG. 1 illustrates a new sleeve bearing with a sensor inserted into the wear liner according to this invention.

The new, unused sleeve bearing is assembled with a shaft which has radius $R_{shaft}$. The shaft is centered in the bearing, concentric with the race, which has a radius $R_{race}$. The sensor conductive electrode is positioned inside the liner, having radius $R_{sensor}$, such that all three are concentric and $R_{race} > R_{sensor} > R_{shaft}$.

We assume the liner has a uniform dielectric constant of $\varepsilon$. The new bearing, with no wear, will have a capacitance $C_{new}$ between the sensor and the shaft, which is given by:

$$C_{new} = \frac{2\pi\varepsilon_0\varepsilon}{\ln\left(\frac{R_{sensor}}{R_{shaft}}\right)}$$

Table 1 shows a calculation of capacitance for a new shaft bearing.

TABLE 1

Calculation of capacitance for new liner in a sleeve bearing

| NEW LINER | | inch | Value | Metric Unit |
|---|---|---|---|---|
| Wear liner thickness | T | 0.012 | 0.00030 | m |
| sensor position | Sp | 0.006 | 0.00015 | m |
| Diameter of Shaft | Dsh | 0.500 | 0.01270 | m |
| Diameter of Race | Dr = Dsh + 2T | 0.524 | 0.01331 | m |
| Diameter of Sensor | Ds = Dsh + 2Sp | 0.512 | 0.01300 | m |
| Bearing Length | L | 0.500 | 0.01270 | m |
| Dielectric constant of liner | e | 2 | 2 | |
| Permittivity of vacuum | e0 | | 8.85E−12 | F/m |
| Radius of shaft | Rsh = Dsh/2 | | 0.00635 | m |
| Radius of race | Rr = Dr/2 | | 0.00665 | m |
| Radius of sensor | Rs = Ds/2 | | 0.00650 | m |
| Capacitance sensor-shaft | C = 2*pi*e*e0/(ln(Rs/Rsh) | | 4689.2 | pF/m |
| Capacitance Bearing, pF | Cb = C*L | | 59.6 | pF |

There will also be capacitance between the sensor electrode and the outer race, but this value should be constant over the life of the bearing. Between the sensor electrode and the moving shaft, there will be wear. Accordingly, the thickness of the wear liner will decrease, and the shaft will exhibit more play. One aspect of this invention is the effect of concentricity on the measured capacitance of a sensor embedded in a wear lining. We recognize two wear modes that could occur, concentric uniform or non-concentric non-uniform.

Figure 1B:
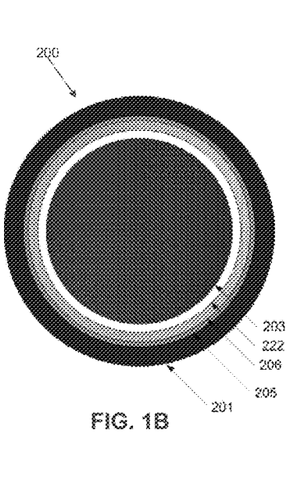
FIG. 1B illustrates a symmetrically worn sleeve bearing with a sensor inserted into a wear liner in accordance with the present invention.

To illustrate uniform wear, we consider a bearing that is worn with perfect symmetry so that some of the wear liner is removed from its entire circumference. Next, we position the shaft in perfect concentricity with the race and sensor electrode. FIG. 1B illustrates a symmetrically worn sleeve bearing with a sensor inserted into the wear liner according to the present invention.

In this arrangement, there are two capacitors in series, one made of air $C_{air}$, and another made from the remaining liner $C_{liner}$. The air gap, having thickness W, will have a capacitance based on the radial gap, $R_{liner} = R_{shaft} + W$. The capacitance of that gap will follow:

$$C_{air} = 2\pi\varepsilon_0 \left( \frac{\varepsilon_{air}}{\ln\left(\frac{(R_{shaft}+W)}{R_{shaft}}\right)} \right)$$

Likewise, the wear liner will have a capacitance based on its thickness, equal to $R_{sensor} - R_{liner}$, or $R_{sensor} - (R_{shaft}+W)$:

$$C_{liner} = 2\pi\varepsilon_0 \left( \frac{\varepsilon_{liner}}{\ln\left(\frac{R_{sensor}}{(R_{shaft}+W)}\right)} \right)$$

The total capacitance, $C_T$, will follow that of two capacitors in series; $C_T = (C_{air} \times C_{liner})/(C_{air}+C_{liner})$. Table 2 shows the result of this calculation.

TABLE 2

Concentrically worn sleeve bearing

| CONCENTRIC WEAR | | inch | Value | Metric Unit |
|---|---|---|---|---|
| Wear liner thickness | T | 0.012 | 0.000305 | m |
| sensor position | Sp | 0.006 | 0.000152 | m |
| Diameter of Shaft | Rsh = Dsh/2 | 0.500 | 0.012700 | m |
| Diameter of Race | Rr = Dr/2 | 0.524 | 0.013310 | m |
| Diameter of Sensor | Rs = Ds/2 | 0.512 | 0.013005 | m |
| Bearing Length | L | 0.500 | 0.012700 | m |
| Dielectric constant of liner | e | 2 | 2 | |
| Permittivity of vacuum | e0 | | 8.85E−12 | F/m |
| Radius of shaft | Rshaft | | 0.00635 | m |
| Radius of race | Rr | | 0.00665 | m |
| Radius of sensor | Rsensor | | 0.00650 | m |
| Wear | W | 0.004 | 0.00010 | m |
| Radius of liner | Rliner = Rshaft + Wear | | 0.00645 | m |
| Capacitance shaft to liner | Cair = 2*pi*e0(1/ln(Rliner/Rshaft)) | | 3503 | pF/m |
| Capacitance liner to electrode | Cliner = 2*pi*e0(e/ln(Rsensor/Rliner)) | | 14180 | pF/m |
| Total Capacitance/m | CT = (Cair*Cliner)/(Cair + Cliner) | | 2809 | pF/m |
| Capacitance | C = CT*L | | 35.7 | pF |

The resulting capacitance is lower than the value calculated in Table 1 for the new bearing. We note that this is the case only if the shaft is held at the center. If loaded, the shaft will be non-concentric and the following example will apply.

Figure 1C:
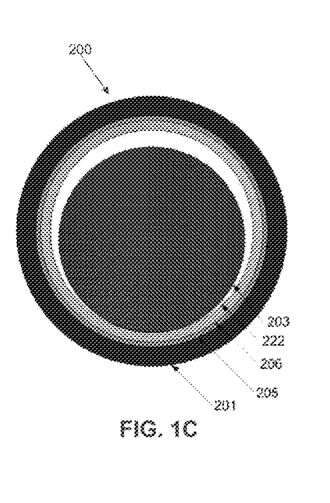
FIG. 1C illustrates a non-concentrically worn sleeve bearing with a sensor inserted into a wear liner in accordance with the present invention.

Next, to illustrate the non-concentric, non-uniform case, we consider a bearing that has been loaded and worn preferentially on one side. The result is that the shaft is no longer concentric with the sensor. FIG. 1C illustrates a non-concentrically worn sleeve bearing with a sensor inserted into the wear liner according to the present invention.

The capacitance of two cylinders eccentrically located one inside the other with radii ($R_{shaft}$) and ($R_{sensor}$), respectively, but with the centers of the two cylinders having a distance (W) apart, will be larger than in the concentric case. Ignoring the replacement of the worn-away dielectric with air, the capacitance would be:

$$C = 2\pi\varepsilon_0\varepsilon \left( \frac{1}{\mathrm{acosh}\left(\frac{-(W^2 - R_{shaft}^2 - R_{sensor}^2)}{2R_{shaft}R_{sensor}}\right)} \right)$$

The capacitance is calculated for an eccentrically worn sleeve bearing in Table 3.

TABLE 3

Non-concentric wear of a sleeve bearing

| WORN LINER | | inch | Value | Metric Unit |
|---|---|---|---|---|
| Wear liner thickness | T | 0.012 | 0.000305 | m |
| sensor position | Sp | 0.006 | 0.000152 | m |
| Diameter of Shaft | Dsh | 0.500 | 0.012700 | m |
| Diameter of Race | Dr = Dsh + 2T | 0.524 | 0.013310 | m |
| Diameter of Sensor | Ds = Dsh + 2Sp | 0.512 | 0.013005 | m |
| Bearing Length | L | 0.500 | 0.012700 | m |
| Dielectric constant of liner | e | 2 | 2 | |
| e0 | e0 | | 8.85E−12 | F/m |

TABLE 3-continued

Non-concentric wear of a sleeve bearing

| WORN LINER | | inch | Value | Metric Unit |
|---|---|---|---|---|
| Radius of shaft | Rsh = Dsh/2 | | 0.006350 | m |
| Radius of race | Rr = Dr/2 | | 0.006655 | m |
| Radius of sensor | Rs = Ds/2 | | 0.006502 | m |
| Eccentric Wear | W | 0.004 | 0.000102 | m |
| Capacitance/m shaft to sensor | C = 2*pi*e*e0*(1/(acosh(-(W^2 - Rsh^2 - Rs^2)/2Rsh*Rs)) | | 6440.4 | pF/m |
| Capacitance of Bearing | Cb = C*L | | 81.8 | pF |

In Table 3, we see that the capacitance is significantly higher for the non-concentric worn bearing than for the new bearing. A notable aspect of this invention is that the capacitance between a metallic shaft and a sensor placed inside or behind the wear liner will increase with concentric or non-concentric wear, as long as the shaft is loaded. The capacitance is an inverse function of the liner thickness. Accordingly, the capacitance increases rapidly as the liner thickness approaches zero.

Between the two previous examples, we expect to find the non-uniform, non-concentric case to be prevalent, as the loading and wear of bearings is rarely uniform. As such, we can relate the wear of a bearing to a measurable increase in capacitance between the shaft and the sensor.

The capacitance measurement can be made at different frequencies. A standard frequency for capacitance measurement is 10 kHz. Measurements taken at a higher frequency improve the sensitivity of the measurement, but also increase the error due to interference. The optimal frequency for accuracy will depend on the electromagnetic interference in the environment surrounding the bearing. The measurement of Q factor, which can be calculated from the active and inductive current components in the sensor, provides information about the status of the liner. If at any point the gap between the sensor and the ball approaches zero, Q will drop rapidly toward zero. It will also be electrically shorted at this point. A Q under 5 indicates that the bearing needs immediate replacement, and a Q above 20 indicates a bearing with good health. The electrical shorting of the sensor and ball can also be used as an indicator that the wear liner has failed in at least one spot, and therefore needs replacement.

Turning again to FIG. 1, FIG. 1A illustrates a new sleeve bearing (without wear) 200, comprising an outer race 201, a movable shaft 203, a wear liner 206 and a sensor 205 inserted into wear liner 206.

FIG. 1B illustrates the sleeve bearing 200 of FIG. 1A after symmetric wear of wear liner 206. The symmetric wear of wear liner 206 results in a worn sleeve bearing 200 having an equal air gap 222 between wear liner 206 and movable shaft 203, with erosion of all wear on sleeve bearing 200 lining up to sensor 205.

FIG. 1C illustrates an asymmetrically, a non-concentrically worn sleeve bearing 200 with a sensor 205, where shaft 203 is closer to sensor 205 in one location than in another location. An air gap 222 is created by the removed material.

Figure 2A:
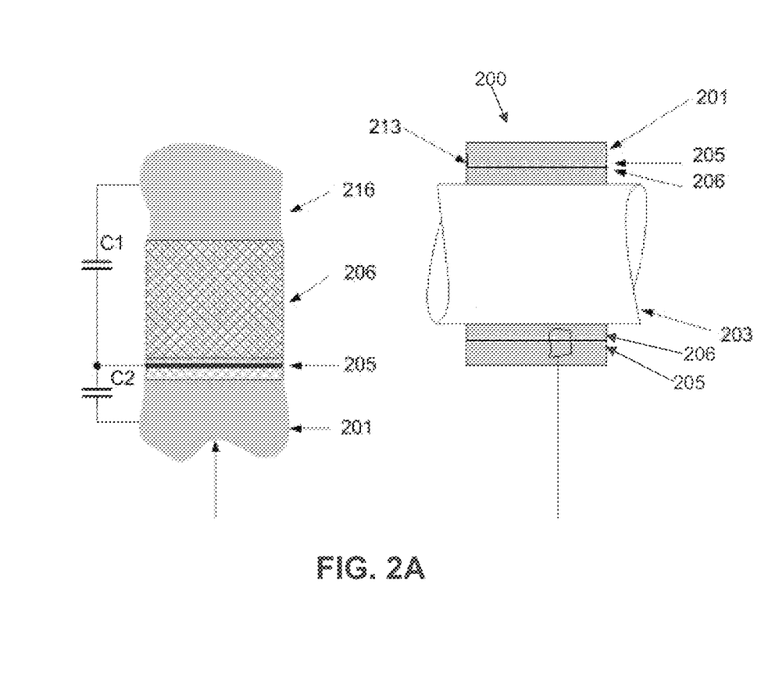
FIGS. 2A-2D illustrate a sleeve bearing with a capacitive sensor inserted into a wear liner in accordance with the present invention, wherein the capacitive sensor is to be measured with a probe contact.
Figure 2B:
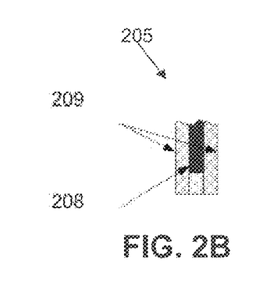
Figure 2C:
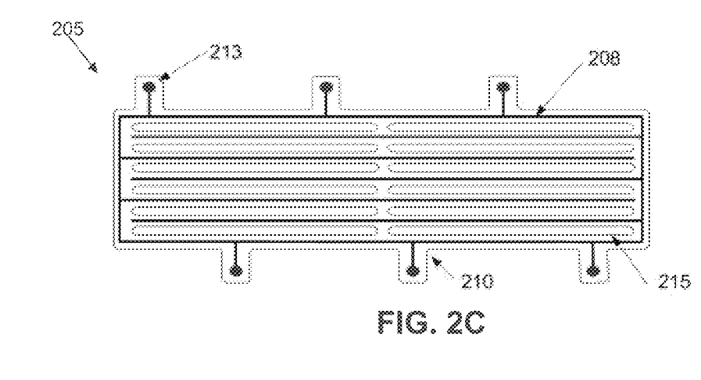
Figure 2D:
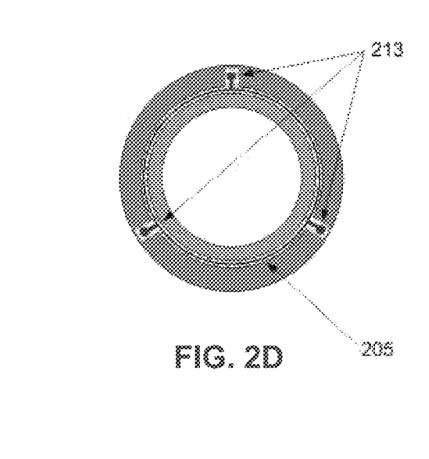

Looking now at FIG. 2A, FIG. 2A illustrates a sensor 205 for a sleeve bearing 200, comprising a race 201, a shaft 203, a sensor 205 and a wear liner 206. Sensor 205 comprises a conductive trace 208 sandwiched between a lower and upper layer of insulating substrate 209 which may be of differing thicknesses (FIG. 2B). When sensor 205 is laid flat (FIG. 2C), conductive trace 208 can be seen in detail, along with tabs 210 that extend from sleeve bearing 200. Slots 215 formed on sensor 205 assist in the flow of adhesive between layers. Electrode pads 213 are positioned on the surface of tabs 210 which can be probed with a capacitance meter to measure the capacitance between one electrode pad and shaft 203 (FIG. 2D).

Figure 3A:
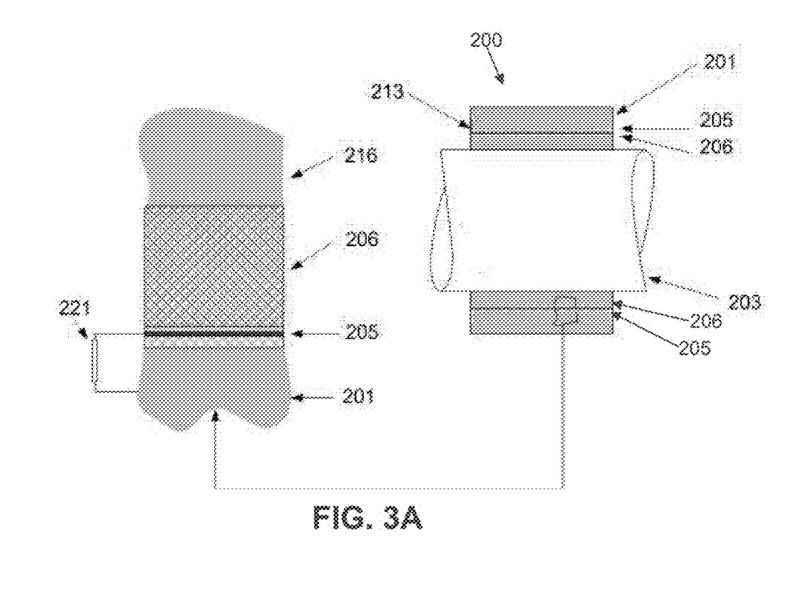
FIGS. 3A-3D illustrate a sleeve bearing with a capacitive sensor inserted into a wear liner in accordance with the present invention, wherein the sleeve bearing comprises an antenna with significant inductance for creating a resonant LC circuit.
Figure 3B:
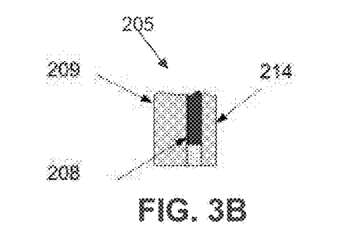
Figure 3C:
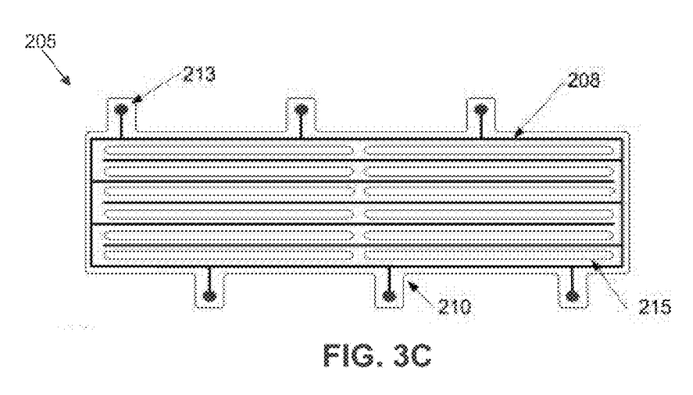
Figure 3D:
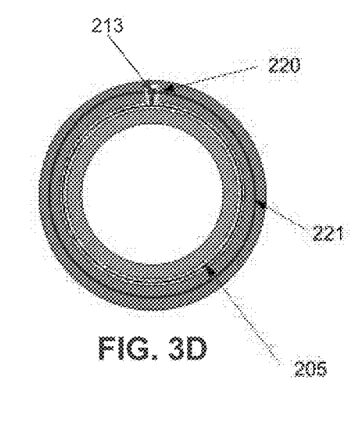

Looking now at FIG. 3A, FIG. 3A illustrates a sensor 205 for a sleeve bearing 200, comprising a race 201, a shaft 203, a sensor 205 and a wear liner 206. Sensor 205 comprises a conductive trace 208 sandwiched between a lower layer of insulating substrate 209 and an upper layer of insulating substrate 214 (FIG. 3B). When sensor 205 is laid flat (FIG. 3C), conductive trace 208 can be seen in detail, along with tabs 210 that extend from sleeve bearing 200. Slots 215 formed on sensor 205 assist in the conformation of the sensor to surface variations, and to flow of adhesive between layers. Electrode pads 213 are positioned on the surface of tabs 210 which can be taken together as a connection point 220 for an antenna 221.

Figure 4A:
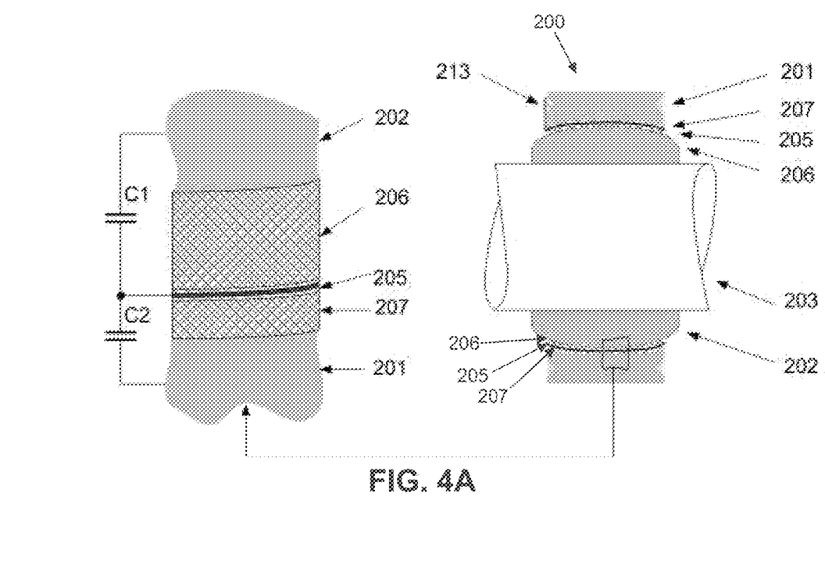
FIGS. 4A-4D illustrate a spherical bearing with a capacitive sensor inserted into a wear liner in accordance with the present invention, wherein the capacitive sensor is to be measured with a probe contact.
Figure 4B:
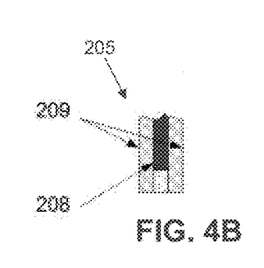
Figure 4C:
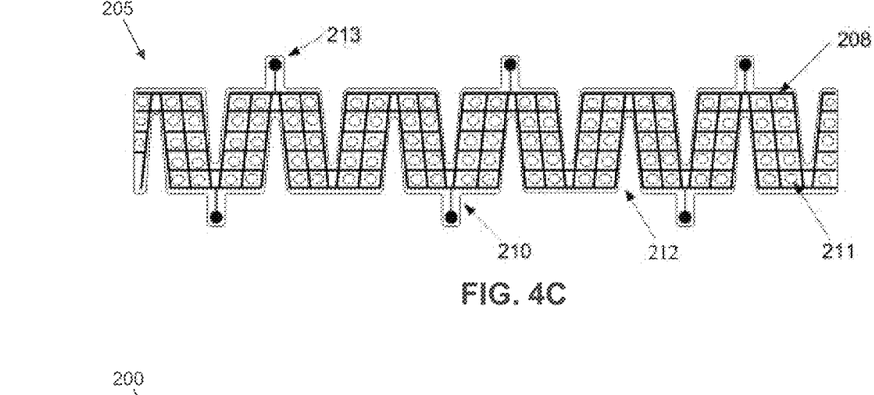
Figure 4D:
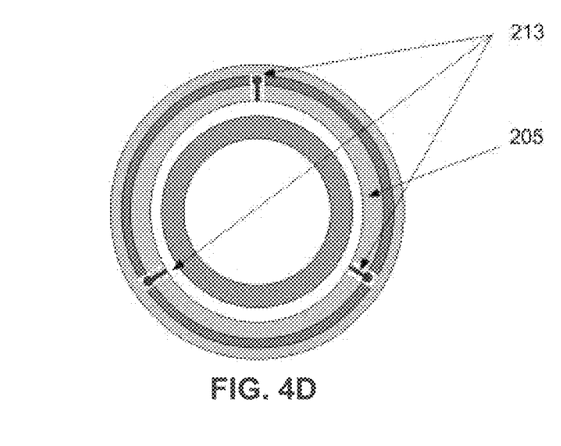

FIG. 4A illustrates a spherical bearing 200 comprising a race 201, a ball 202, a shaft 203, a sensor 205, a wear liner 206 and an insulator 207. Sensor 205 comprises a conductive trace 208 sandwiched between two layers of insulating substrate 209 (FIG. 4B). When sensor 205 is laid flat (FIG. 4C), conductive trace 208 can be seen in detail, along with tabs 210 that extend from sleeve bearing 200. Holes 211 formed on sensor 205 assist in the flow of adhesive between layers. Strain relief cuts 212 formed on sensor 205 enable sensor 205 to deform into a more conformal shape. Electrode pads 213 are positioned on the surface of tabs 210 for the interrogation of sensor 205 (FIG. 4D). Viewed end on, after installation, electrode pads 213 may be touched with one probe of a capacitance meter.

Figures 5A, 5B:
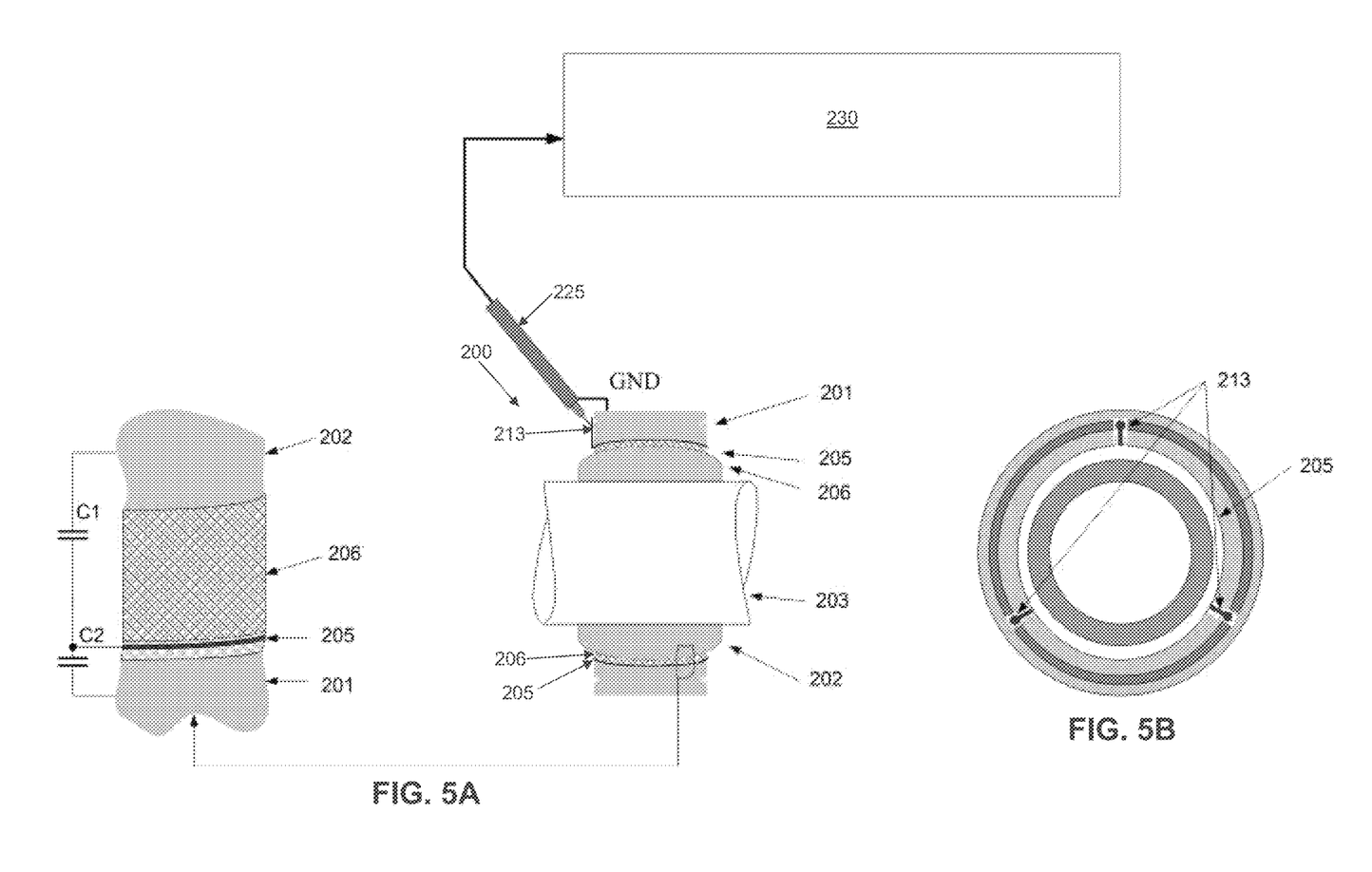
FIGS. 5A and 5B illustrate a method of interrogating a capacitive sensor inserted into a wear liner of a spherical bearing in accordance with the present invention, using a capacitance meter.

Looking now at FIGS. 5A and 5B, FIGS. 5A and 5B, illustrate a method of interrogating sensor 205. As shown in FIG. 5A, a probe 225 of a precision capacitance meter 230 makes contact with an electrode pad 213 on the circumference of spherical bearing 200. Assuming that race 201 and shaft 203 are both conductive and electrically connected elsewhere, the capacitance measured by the precision capacitance meter shall be comprised of the capacitance between ball 202 and sensor 205, which is electrically in series with the capacitance between sensor 205 and race 201.

Figure 6A:
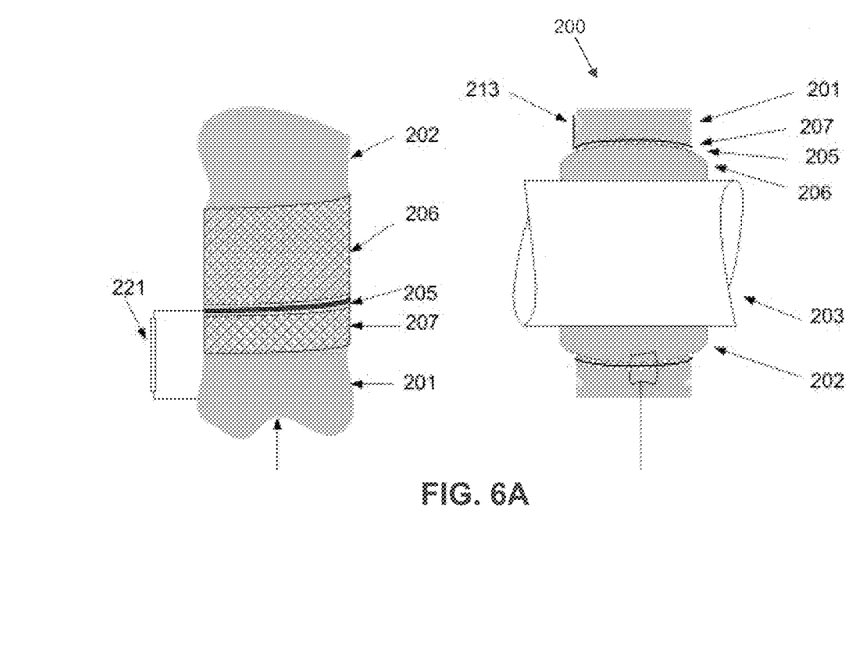
FIGS. 6A-6D illustrate a spherical bearing with a capacitive sensor inserted into a wear liner in accordance with the present invention, and wherein the spherical bearing comprises an antenna with significant inductance for creating a resonant LC circuit.
Figure 6B:
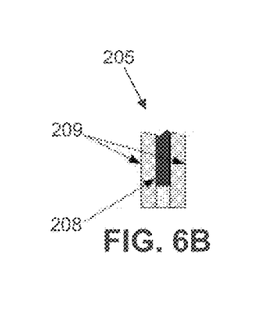
Figure 6C:
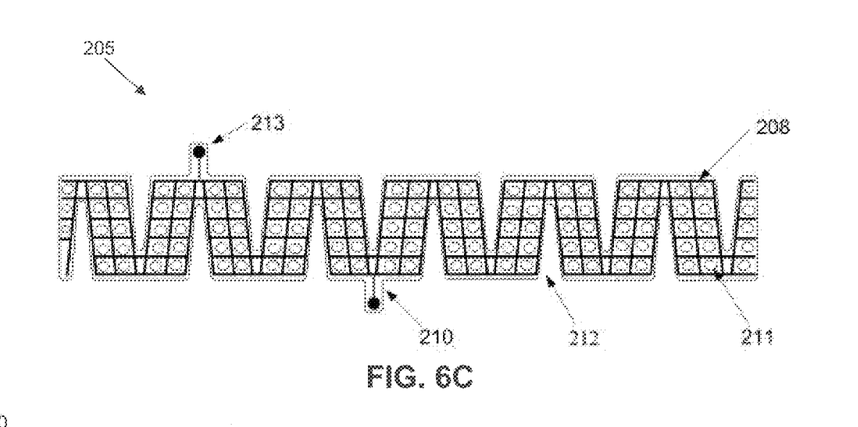
Figure 6D:
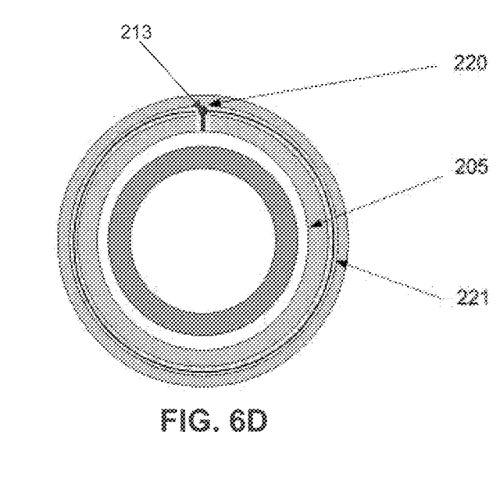

FIG. 6A illustrates a spherical bearing 200 comprising a race 201, a ball 202, a shaft 203, a sensor 205, a wear liner 206 and an insulator 207. Sensor 205 comprises a conductive trace 208 sandwiched between two layers of insulating substrate 209 (FIG. 6B). When sensor 205 is laid flat (FIG. 6C), conductive trace 208 can be seen in detail, along with tabs 210 that extend from sleeve bearing 200. Holes 211 formed on sensor 205 assist in the flow of adhesive between layers. Strain relief cuts 212 formed on sensor 205 enable sensor 205 to deform into a more conformal shape. Electrode pads 213 are positioned on the surface of tabs 210 for the interrogation of the sensor (FIG. 4D). Viewed end on, after installation, tabs 210 and electrode pads 213 are connected at a point 220 to an antenna 221, which may be mounted on the face of race 201.

Figures 7A, 7B:
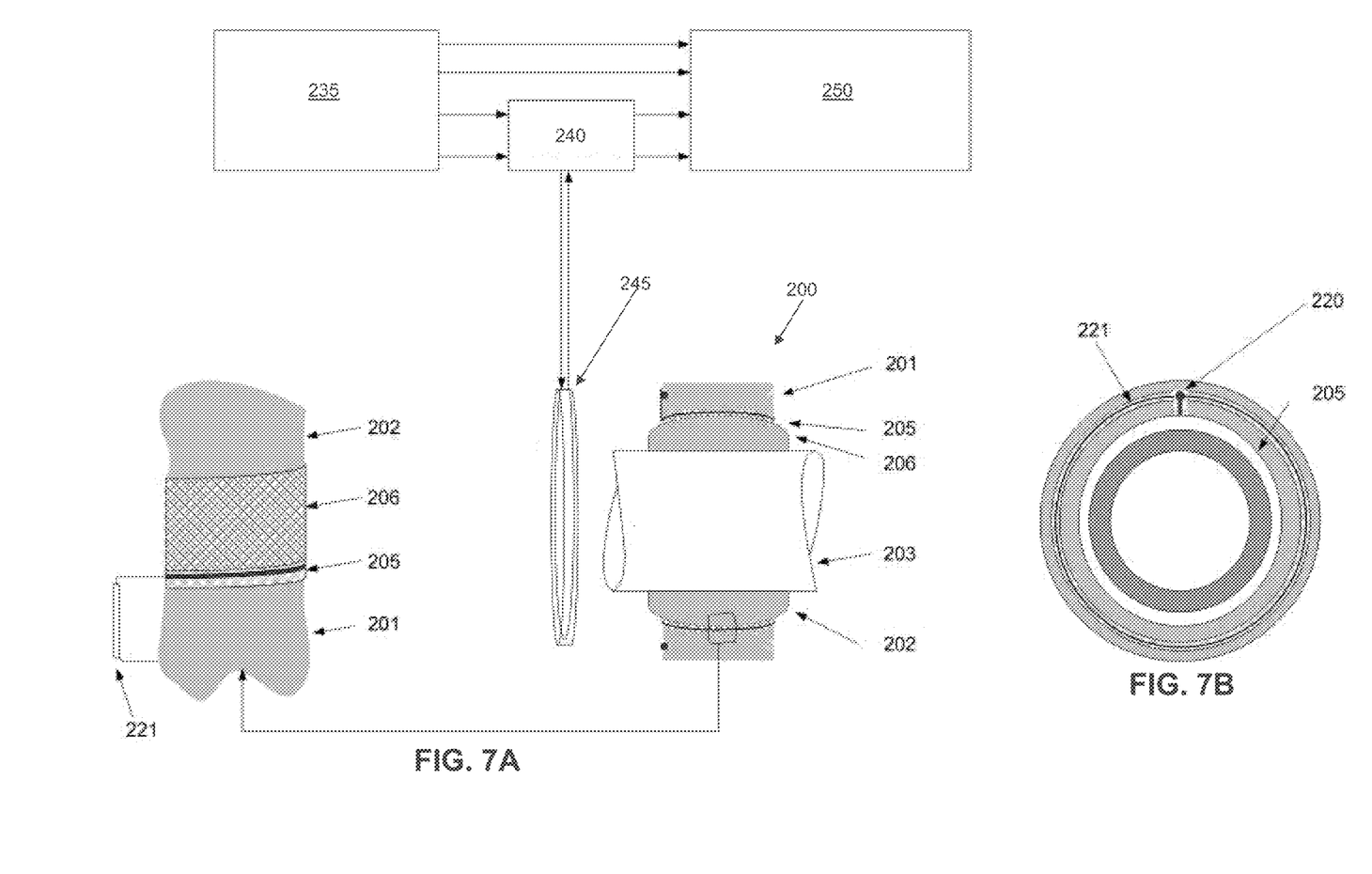
FIGS. 7A and 7B illustrate a method of interrogating the capacitive sensor described in FIGS. 6A-6D with a tracking generator, matching network, interrogating antenna, and a spectrum analyzer.

Looking now at FIGS. 7A and 7B, FIGS. 7A and 7B illustrate a method of interrogating sensor 205 wirelessly. A signal produced by a tracking generator 235 is coupled through a matching network 240 to a loop antenna 245, which interacts with sensor antenna 221, for measuring bearing wear remotely. The output frequency of tracking generator 235 is varied over time, and at one moment will match the frequency of the LC circuit created by the sensor's capacitance and the antenna's inductance. At that moment, a spectrum analyzer 250 will detect the resonance frequency. The shift in resonant frequency shift from the change in sensor capacitance will correspond to the reduction in the wear liner thickness. Preferably, sensor antenna 221 may be placed in a detent, which is a circumferential groove in bearing race 201.

Figure 8A:
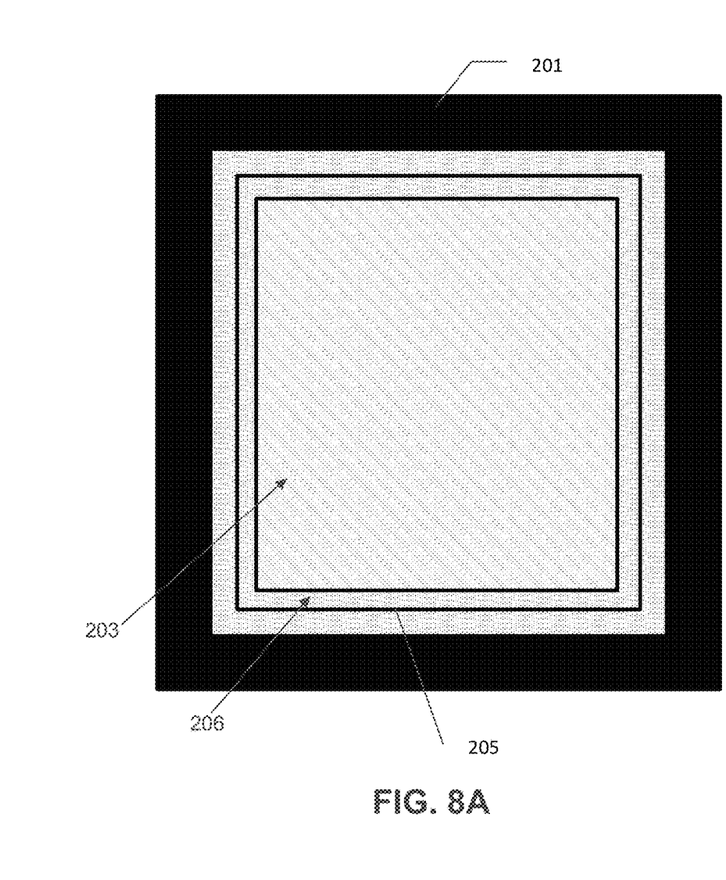
FIG. 8A illustrates a new square telescoping bearing with a sensor inserted into a wear liner in accordance with the present invention.

FIG. 8A illustrates a new square telescoping bearing with a sensor inserted into the wear liner in accordance with the present invention.

Figure 8B:
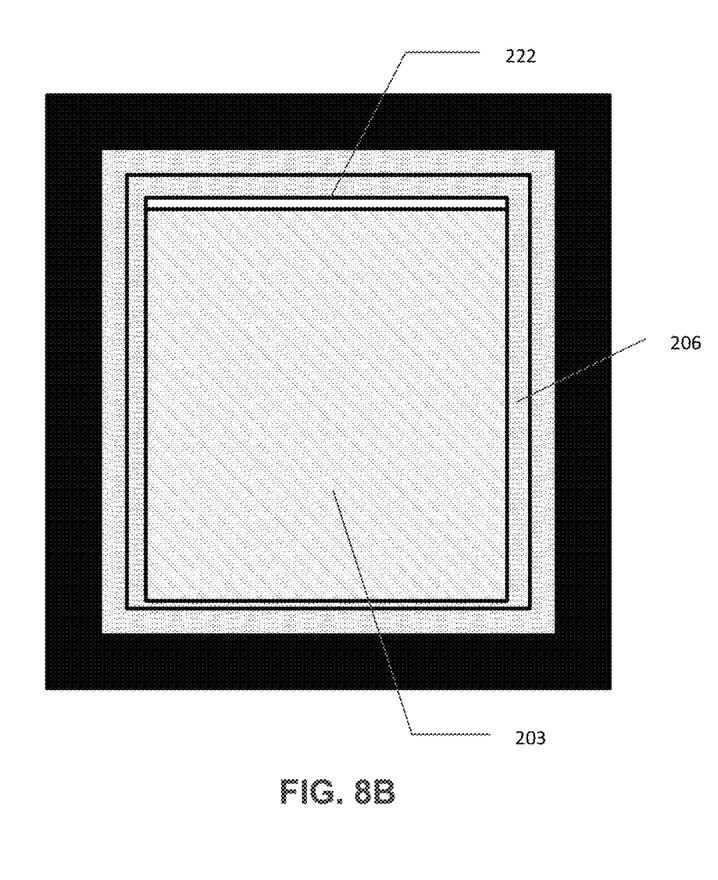
FIG. 8B illustrates a worn square telescoping bearing with a sensor inserted into a wear liner in accordance with the present invention.

FIG. 8B illustrates a worn square telescoping bearing with a sensor inserted into the wear liner in accordance with the present invention.

Figure 9A:
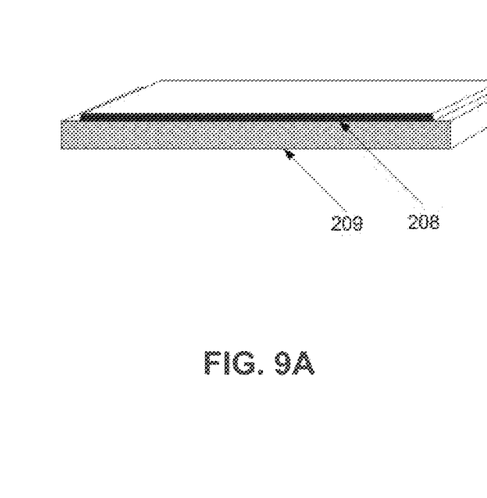
FIGS. 9A-9C depict a process flow for producing the wear liner of the present invention.
Figure 9B:
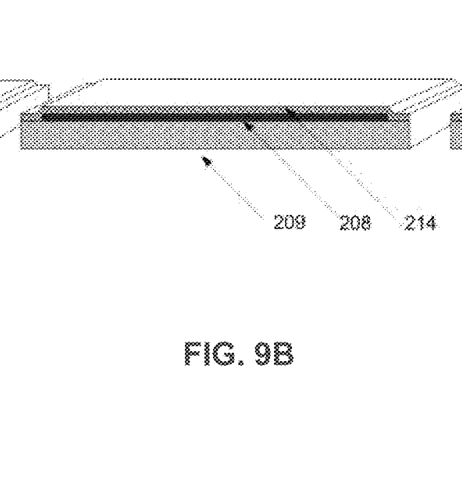
Figure 9C:
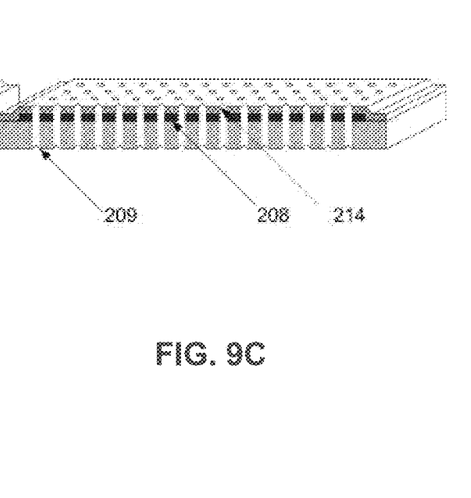

One illustrative procedure for producing a device according to the present invention is shown in FIGS. 9A-9C. In FIG. 9A, there is shown an insulating substrate 209 with a metallic coating 208. In FIG. 9B, a second layer of insulator 214 is applied to sandwich the electrode, which may be patterned. In FIG. 9C, at least one hole or a pattern is cut out, producing a sensor that can be inserted into a bearing. Holes in the sheet are expected to improve the bonding with the substrate.

Turning back to FIG. 8A, FIG. 8A is an end-view of a new, un-worn telescoping structure comprising an outer sleeve 201, an inner shaft 203 and a wear lining 206, which has been instrumented with a sensor 205 part-way through wear lining 206. In FIG. 8B, wear liner 206 has been worn, leaving an air gap 222 and a reduced lining thickness on one side. The capacitance of this system can be modeled as the sum of the four parallel plate capacitors. Capacitance in this system is equal to the product of the permittivity of free space $\epsilon_0$, the dielectric constant $\epsilon$ and the area A divided by the distance d: $C=\epsilon\epsilon_0 A/d$.

Comparing FIG. 8A to FIG. 8B, the lining thickness on the sides is unchanged, but in FIG. 8B the upper and lower distances are changed. At the bottom, the thickness of wear lining 206 has been reduced by wear, and a corresponding air gap 222 has opened up above shaft 203 at the top. The upper capacitor will have a lower value than before as the distance between shaft 203 and sensor 205 is increased by air gap 222. The lower capacitor will have a much higher value than before, as it has a distance between shaft 203 and sensor 205 that is reduced by the same distance as air gap 222. The increase in capacitance for the lower capacitor will more than make up for the decrease in capacitance for the upper capacitor. This is clear because the function 1/d is nonlinear. It approaches infinity as the quantity 'd' gets small, and it approaches zero as 'd' gets large.

We note that a similar type of measurement could be made if the wear liner material was conductive, and the resistance was measured as a function of wear.

There are two methods to measure the capacitance of the sensor. The first is to measure the value directly with a probe and a capacitance meter. The other alternative is to measure the resonant frequency of the combination of the sensor's capacitance and the attached antenna's inductance. A similar measurement could be implemented using an inductive sensor and a distributed capacitor to create the resonant circuit.

The preceding examples should be construed as non-limiting, as other methods of implementing the sensor are possible. Also, other methods can be used to measure the wear in addition to capacitance, including inductance and resistance.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A wear sensor comprising:
an insulating substrate having a top surface and a bottom surface;
a conductive electrode formed on said top surface of said insulating substrate;
an insulating wear lining material having a first side secured to said top surface of said insulating substrate and conductive electrode, an opposite second side that will be worn down by relative motion between the wear sensor and a moving component;
one or more contact points where the capacitance between the electrode and the moving component is measured; and
a capacitance meter for measuring the capacitance between the electrode and the moving component so as to identify wear in the insulating wear lining material without requiring current to flow between the electrode and the moving component.

2. A wear sensor according to claim 1 wherein inductance is the electrical property measured.

3. A wear sensor according to claim 1 wherein the Q factor of the sensor is the electrical property measured.

4. A wear sensor according to claim 1 wherein the insulating substrate is flexible.

5. A wear sensor according to claim 1 wherein the insulating substrate is also a wear material.

6. A wear sensor according to claim 1 wherein the wear sensor is implemented in a set of nested, telescoping tubes.

7. A wear sensor according to claim 6 wherein said electrical property is resistance.

8. A wear sensor according to claim 1 wherein the wear sensor is implemented in a shaft bearing.

9. A wear sensor according to claim 1 wherein the wear sensor comprises a surface to measure the thickness or dielectric constant of a coating.

10. A wear sensor according to claim 1 wherein the wear sensor is interrogated by measuring the resonant frequency or Q factor of a circuit.

11. A wear sensor according to claim 1 wherein the wear sensor is implemented with an inductor to create an LC circuit with a resonant frequency and Q factor.

12. A wear sensor according to claim 11 wherein the wear sensor is implemented with an inductive antenna to create an LC circuit with a resonant frequency and Q factor.

13. A wear sensor according to claim 1 wherein the wear sensor comprises a resistor to create an RC circuit with a resonant frequency and Q factor.

14. A wear sensor according to claim 1 wherein the wear sensor comprises an antenna to enable wireless interrogation of the wear sensor.

15. A wear sensor according to claim 1 wherein the wear sensor is implemented in a spherical bearing.

* * * * *

UNITED STATES PATENT AND TRADEMARK OFFICE
CERTIFICATE OF CORRECTION

PATENT NO. : 9,797,850 B2
APPLICATION NO. : 14/054447
DATED : October 24, 2017
INVENTOR(S) : Iosif Izrailit and David L. Carnahan It is certified that error appears in the above-identified patent and that said Letters Patent is hereby corrected as shown below:

In the Specification

At Column 1, Line 4, the statement --This invention was made with Government support under N68335-13-C-0203 awarded by the Department of the Navy. The Government has certain rights in this invention.-- should be inserted.

Signed and Sealed this
Twenty-seventh Day of March, 2018

Andrei Iancu
*Director of the United States Patent and Trademark Office*